(12) United States Patent
Bajwa

(10) Patent No.: US 12,697,242 B2
(45) Date of Patent: Aug. 4, 2026

(54) PAEDIATRIC AND ADULT FIXATOR HAVING A PRESSURE ELEMENT

(71) Applicant: Cambridge Orthopaedic Labs Limited, Leicestershire (GB)

(72) Inventor: Ali Bajwa, Leicestershire (GB)

(73) Assignee: CAMBRIDGE ORTHOPAEDIC LABS LIMITED, Leicestershire (GB)

( * ) Notice: Subject to any disclaimer, the term of this patent is extended or adjusted under 35 U.S.C. 154(b) by 148 days.

(21) Appl. No.: 18/464,543

(22) Filed: Sep. 11, 2023

(65) Prior Publication Data

US 2025/0082489 A1 Mar. 13, 2025

(51) Int. Cl.
A61F 5/058 (2006.01)

(52) U.S. Cl.
CPC ...... A61F 5/05841 (2013.01); A61F 5/05825 (2013.01)

(58) Field of Classification Search
CPC .... A61F 5/04; A61F 5/042; A61F 5/05; A61F 5/0585; A61F 5/05858; A61F 5/05866; A61F 5/0102; A61F 5/05841; A61F 5/05825
See application file for complete search history.

(56) References Cited

U.S. PATENT DOCUMENTS

| | | | | |
|---|---|---|---|---|
| 1,384,257 A | * | 7/1921 | Hilgers | A61F 5/04 |
| | | | | 602/25 |
| 1,517,915 A | * | 12/1924 | Masland | A61F 5/0585 |
| | | | | 606/54 |
| 5,065,770 A | * | 11/1991 | Palfray | A61B 5/107 |
| | | | | 600/587 |
| 5,876,333 A | * | 3/1999 | Bigliani | A61B 17/02 |
| | | | | 600/231 |
| 7,004,943 B2 | * | 2/2006 | Ferrante | A61B 17/645 |
| | | | | 606/59 |
| 8,147,491 B2 | * | 4/2012 | Lavi | A61B 17/6458 |
| | | | | 606/54 |
| 9,320,638 B2 | * | 4/2016 | Ali | A61F 5/04 |
| 2011/0301610 A1 | * | 12/2011 | Ali | A61B 17/00 |
| | | | | 606/74 |
| 2017/0119570 A1 | | 5/2017 | Beck | |
| 2022/0022917 A1 | | 1/2022 | Giordano | |

FOREIGN PATENT DOCUMENTS

| | | |
|---|---|---|
| WO | 2010094971 A2 | 8/2010 |
| WO | 2020148715 A1 | 7/2020 |

OTHER PUBLICATIONS

International Search Report for international application No. PCT/EP2024/074741, dated Nov. 29, 2024, 14 pages.

* cited by examiner

*Primary Examiner* — Kari K Rodriquez
(74) *Attorney, Agent, or Firm* — Tarolli, Sundheim, Covell & Tummino LLP

(57) ABSTRACT

A non-invasive fixator for use in treatment of bone fractures and other injuries is described. The fixator includes articulated bracelets each formed of a plurality of linking elements arranged in a plurality of rows. The elements have complementary linking means to permit linking the rows of elements together in an articulated or fixed relationship. The bracelets are also provided with further components and connector elements which can apply pressure to a fracture or injury site. Certain embodiments are useful for either paediatric or adult use. Also described herein are improvements to certain connector pieces of use in the fixator. Also described is a novel polylattice membrane for medical and therapeutic use.

21 Claims, 10 Drawing Sheets

Link with bridge of existing Middle Links and Outside links

Bridges of various fixed depths

Bridge fitted between cuffs

Existing Rod to Rod Connector with short rod and pad

Adjustable Bridge – adjusted with screw and nut

SECTION A-A
SCALE 1 : 1

Adjustable Bridge fitted onto Middle link of each cuff with Locking Thread and screws 12-5515
M4x25 Torx Pan
Head Screw 12-5514
Spring 12-5513
Sprung Top 12-5512
Rod Fixator Clamp 12-5512
Rod Fixator Clamp 12-5511
Joint Bottom 12-5510
Locking Thred

614

616

618

606

608

610

612

302

SECTION A-A

A

A

Screw thread
to be deformed after insertion
to prevent removal 802
804

Surface
Layer

806

Spacer
Yarn

Surface
Layer

DETAIL B
SCALE 4 : 1

200

Grip
Material

Surface
Layer

808

SECTION A-A
SCALE 2 : 1

A

A

PAEDIATRIC AND ADULT FIXATOR HAVING A PRESSURE ELEMENT

FIELD OF THE INVENTION

The present invention relates to a non-invasive external fixator particularly suitable for fracture fixation. Certain embodiments relate to a fixator having a pressure plate for exerting pressure on a fracture or other injury site. Certain embodiments are useful for either paediatric or adult use. Other embodiments are apparent from the following description.

BACKGROUND OF THE INVENTION

A non-invasive external fixator is described in WO 2010/094971, the contents of which are incorporated by reference. That fixator includes a first and second articulated bracelet which can be located around the circumference of a patient limb. Each bracelet is formed of a plurality of elements arranged in a plurality of rows, wherein said elements have complementary linking means to permit linking said rows of elements together in an interchangeably articulated or fixed relationship, wherein one or more of said plurality of elements comprises means for receiving and engaging at least a portion of a connecting device such that the position of the connecting device can be altered around the bracelet or the limb that it is mounted on, at least one articulated connecting device on each of said first and second bracelet; a rod connecting said at least one articulated connecting device on said first bracelet to said at least one articulated connecting device on said second bracelet and a hinge device.

Thus, during assembly of the bracelet about a patient's limb for example, the elements can be linked in an articulated relationship to facilitate correct sizing. Once appropriately assembled, the elements can be fixed to provide support for the limb during the healing process. The bracelet can therefore be made to fit snugly around the patient's limb by adjusting its length and curvature in the process of fitting, without the need for straps or other encircling bands. The bracelets can be made substantially rigid by simple application of pressure on the built-in locking mechanism that involves engaging the elements of the bracelet. Stability is provided by virtue of using a plurality of rows of elements that can be made substantially rigid when conforming in appropriate shape around the limb. Thus, the bracelet is capable of changing from a substantially rigid and fixed state to a flexible and articulated state. The bracelet and its elements can be manipulated to conform to the desired shape (circular, oval, etc) and length.

The articulated connecting devices will serve to connect each bracelet to a rod, with the rod spanning the fracture or other injury site and maintaining the bracelets in alignment, to reduce or prevent fracture movement.

An example of the device described in WO2010/094971 is shown in FIG. 1, with an enlarged view of a portion of a bracelet shown in FIG. 2. The features are described in more detail below.

SUMMARY OF THE INVENTION

The present inventor has identified a number of improvements and modifications to fixators of the type described in WO2010/094971, and to their individual elements. The invention expands on the previous fixator design, and allows use of the improved fixator in a number of new fields, including greenstick fractures in paediatric patients, and treatment of deformed fractures, both of which may benefit from the application of pressure to the injury site. In particular, the following features are described herein, and the present invention may relate to each of these, whether in isolation or in combination, either as an individual element or as a component of a fixator. Certain of the improvements relate to components which can interconnect with the existing bracelets, either by modification of existing links or by interacting with links. Such components may be used in order to apply pressure to a fracture or injury site. Also described herein are improvements to certain connector pieces of use in the fixator. The inventor further describes a novel polylattice membrane for medical and therapeutic use.

According to a first aspect of the present invention, there is provided a non-invasive fixator for fixing a fracture or soft tissue injury, the fixator comprising:

first and second articulated bracelets, each of which is for location around the circumference of a patient's limb;

each articulated bracelet comprising a plurality of linking elements located in a plurality of rows, wherein said linking elements have complementary linking means to permit linking said rows of linking elements together in an interchangeably articulated or fixed relationship;

at least one linking element in each bracelet comprising a connector element having a portion extending laterally from one of said rows, and forming a further linking means to permit linking of further elements to the bracelet in a direction generally perpendicular to the direction of the rows.

This arrangement provides for additional elements to be connected to the bracelets, extending perpendicular to the direction of the bracelet. In preferred embodiments, the connector element may comprise a tri-armed piece; for example, a T-piece. Each arm of the tri-armed or T piece may comprise a linking means; this may permit, for example, a first arm of the T piece to connect to the body of the bracelet, while the second and third arms are free to permit additional connections.

As used herein the term 'articulated' refers to a configuration in which relative motion is allowed to occur, while 'fixed' refers to a configuration in which relative motion is substantially restricted. It will be understood that in an articulated configuration there may be some degree of resistance to relative motion, for example sufficient for the articulated bracelet to holds its shape without sagging.

The fixator may further comprise additional linking elements connected to the connector element and extending between the first and second articulated bracelets. This forms a connection or bridge between the bracelets. In preferred embodiments, the additional linking elements each comprise complementary linking means to permit linking said linking elements together in an interchangeably articulated or fixed relationship. This allows the bridge to be fixed in position in much the same way as the bracelets. This is particularly advantageous when the linking elements of the bridge are arranged and fixed in position so as to extend between and below the first and second bracelets—that is, when worn on a limb, the bracelets may circle the limb relatively loosely, while the bridge will provide pressure against the limb by virtue of extending below the bracelets. It can be beneficial with some forms of fracture or soft tissue injury to be able to apply pressure to the injury site (for example, improving healing or reducing relative movement between parts).

In some embodiments, one or more of said plurality of linking elements comprises means for receiving and engaging at least a portion of a connecting device such that the position of the connecting device can be altered around the bracelet or the limb that it is mounted on. The fixator may further comprise at least one articulated connecting device received in and engaged to each of said first and second bracelet; a rod connecting said at least one articulated connecting device on said first bracelet to said at least one articulated connecting device on said second bracelet. This provides a further connection between the bracelets, either in addition to or instead of, the bridge. The connecting devices and rods are useful to provide anchor points for the fixator and bracelets which may resist torque or compression forces which would otherwise risk movement of the fixator. They may be considered an alternative to conventional fixator pins which are typically secured to a patient's bone. Articulated connecting devices may permit movement in one, two, or preferably three planes. In the context of the present invention, the term "connecting device" refers to any structure that can be used to connect one component to another component. Preferably, the connecting device can be received and engaged without the need for technical processing such as welding and soldering. An embodiment of an exemplary connecting device is described herein, though it will be appreciated that other suitable connecting devices could also be used.

In some embodiments, the linking elements of adjacent rows are offset relative to one another in a row direction.

The bracelet may comprise a central row of elements and two outer rows of elements. One or more elements of said central row may comprise said means for receiving and engaging at least a portion of a connecting device such that the position of the connecting device can be altered around the bracelet or the limb that it is mounted on. Said means for receiving and engaging may comprise a channel. In embodiments, said channel is partially enclosed by inwardly extending segments. In embodiments, said channel has at least one open end.

In some embodiments said linking means comprise: at least one arcuate projection extending laterally on a first of said elements; and at least one arcuate slot for receiving said arcuate projection in a second of said elements; wherein said first and second elements belong to adjacent rows. The arc of said arcuate slot may be greater than the arc of said arcuate projection. In embodiments, a first arcuate surface of said arcuate projection is provided with one or more ridge-like teeth, and a first arcuate surface of said slot is provided with one or more cooperating ridge-like teeth. A second arcuate surface of said arcuate projection may be provided with one or more arcuate grooves. A second arcuate surface of said slot may be provided with a latch extending laterally to said row direction. In some embodiments, said plurality of linking elements comprise first and second kinds of elements, said first kind of elements having a plurality of said arcuate projections and said second kind of elements having a plurality of said slots.

In preferred embodiments, said plurality of linking elements is made of radiolucent material.

In preferred embodiments, the articulated connecting device comprises a pair of clamp members, each member having a channel that can be aligned in opposed relationship with one another to form a hole for receiving a rod, at least one of said pair of clamp members having a part-cylindrical portion for mating with a complementary part-cylindrical portion of a support member, said support member being mountable on, or integral with, a spacer portion of a base, wherein said pair of clamp members, said support member and said base are releasably secured together, for example by a pin. The base is designed to be received in and engaged with a portion of the bracelet, for example, by the base and the bracelet having cooperating shaped members. Articulated connecting devices may permit movement in one, two, or preferably three planes. This design permits rotation in a first plane by movement of the base, and movement in second and third planes by movement of the clamp and support members at the part-cylindrical portions.

In embodiments one or more cooperating surfaces of the connecting device may include a ridged or otherwise textured surface. By "cooperating surfaces" is meant those surfaces of the individual components of the connecting device which interact or are in contact with one another. For example, a ridged surface may be provided on the part-cylindrical portions of the clamp and support members; and/or on the support member and the base. These surfaces provide resistance to movement of the components of the connecting device, and also provide tactile feedback to a user when adjusting the connecting device.

In preferred embodiments, the channel is offset from a central axis of said coupling device, so that the pin runs centrally through the components. In preferred embodiments the base is slidably receivable in a channel of an element of the bracelet.

The fixator may also comprise a cross-linking device. In a preferred embodiment, the cross-linking device comprises first and second pairs of clamp members, each member having a channel that can be aligned in opposed relationship with the channel of its paired member to form a hole for receiving a rod, said first and second pairs being releasably secured together back-to-back by a pin. This cross-linking device permits connections of two rods, one being received in each hole. As with the connecting device, one or more cooperating surfaces may be provided with ridges or other textured surface.

In some embodiments, the fixator may further comprise a hinge device. The hinge device may comprise a first hinge part having a pair of spaced first and second ring members; a second hinge part having a third ring member pivotably accommodated between said first and second ring members, said third ring member having inwardly directed teeth formed on an inner circumferential surface thereof; a third hinge part comprising first and second cylindrical members extending through said first and second ring members respectively, each of said first and second cylindrical members have outwardly directed teeth formed on an outer circumferential surface thereof, for engaging with said inwardly directed teeth of said third ring member; and a pin for releasably securing together said first, second and third hinge parts wherein said members are made of substantially radiolucent material and said pin is made of substantially radiopaque material and wherein the hinge permits movements in all planes. In some embodiments the hinge may be selectively lockable in place; for example, the hinge may include a locking pin which can be moved to align with a corresponding opening which then locks the hinge in position.

In some embodiments, the bracelets may comprise an adjustable closure. For example, this may take the form of a toothed strip which engages with a corresponding ratcheted fastener to secure the bracelet in a closed loop. Alternatively, a hook-and-loop type fastener, fasteners, or other arrangement may be used. This permits use of a single sized bracelet on limbs of varying sizes without the need to alter the number of elements in the bracelet. An advantage of a ratcheted-type fastener is that the bracelet may be adjusted to the correct size before being locked in place, and the fastener may prevent the bracelet being accidentally opened by a patient.

In some embodiments, the bridge function may be provided by an alternative means. For example, the fixator may comprise a fixed bridge connector having a fixed shape (in contrast to a bridge formed from articulated elements) connected to the first and second bracelets and extending perpendicularly to the direction of the rows. The fixed shape may be stepped in profile, to provide a portion extending below the height of the bracelets; this will provide the desired force against the limb. The fixed bridge connector may be connected to the bracelets via connector elements, as described herein. Alternatively, a fixed bridge connector may replace at least one linking element in at least one bracelet.

In some embodiments, the bridge function may be provided by a first rod extending between the first and second bracelets, and affixed to each bracelet, in combination with a further rod affixed to the first rod and arranged perpendicularly thereto; the further rod having a footplate extending generally parallel to the first rod and arranged, in use, to contact the limb of a patient. The height of the footplate may be adjustable, for example by altering the relative location of the further rod with respect to the first rod. In embodiments, the first rod may be affixed to the bracelets via connector elements and/or connecting devices as described herein. Alternatively, the rod may include fittings such as screws, bolts, clips, etc allowing such fixing directly to the bracelet. In embodiments, the further rod may be affixed to the first rod via a connecting device as described herein. This may allow the height of the footplate to be adjusted by moving the rod with respect to the connecting device. Alternatively, the further rod may be threaded and received within a corresponding threaded opening in the first rod; the height may then be adjusted by rotation of the relevant pieces. In some instances, this rod arrangement may be used with prior art fixators (for example, as described in WO2010/094971).

The fixator may further comprise a cushioning fabric disposed within one or more of the bracelets, and arranged to, in use, contact a patient's limb. Wearing bracelets may be uncomfortable for some users, and so this cushioning fabric may reduce such discomfort. Further, the cushioning effect and the ability of the fabric to compress slightly will potentially help to avoid constricting blood flow in the event that the patient experiences swelling at or near an injury site. In preferred embodiments, the cushioning fabric is a polylattice membrane comprising a non-woven spacer yarn layer disposed between outer surface fabric layers. The spacer layer comprises yarn threads extending generally between the outer layers so as to provide a cushion effect. Preferably the spacer layer is thicker than the surface layers; preferably the spacer layer is more than 2, 3, or 4 times thicker than each surface layer. In a most preferred embodiment, the surface:spacer:surface layer thicknesses are 1:4:1. The yarn threads of the spacer layer may comprise a polymer material (eg, a clinical grade polymer material); for example, polypropylene; these may be around 0.1 mm diameter. The surface layers may comprise a knitted or woven fabric. This may be a polymer fabric, eg a clinical grade polymer fabric. In embodiments, the surface layers comprise a texturised polyester/polyamide mix; preferably of around 10 wales or courses per cm. In embodiments, the weight of the polylattice membrane is around 500 gsm. The polylattice membrane may further comprise a grip material disposed on the outside of one or both of the surface layers; this may improve adhesion to a user's limb. The grip material may comprise a polymer; for example, may be a silicone material. The grip material may be patterned to further improve adhesion.

In a further aspect of the invention, there is provided a cushioning fabric in the form of a polylattice membrane comprising a non-woven spacer yarn layer disposed between outer surface fabric layers. The spacer layer comprises yarn threads extending generally between the outer layers so as to provide a cushion effect. Preferably the spacer layer is thicker than the surface layers; preferably the spacer layer is more than 2, 3, or 4 times thicker than each surface layer. In a most preferred embodiment, the surface:spacer:surface layer thicknesses are 1:4:1. The yarn threads of the spacer layer may comprise a polymer material (eg, a clinical grade polymer material); for example, polypropylene; these may be around 0.1 mm diameter. The surface layers may comprise a knitted or woven fabric. This may be a polymer fabric, eg a clinical grade polymer fabric. In embodiments, the surface layers comprise a texturised polyester/polyamide mix; preferably of around 10 wales or courses per cm. In embodiments, the weight of the polylattice membrane is around 500 gsm. The polylattice membrane may further comprise a grip material disposed on the outside of one or both of the surface layers; this may improve adhesion to a user's limb. The grip material may comprise a polymer; for example, may be a silicone material. The grip material may be patterned to further improve adhesion.

In a yet further aspect of the invention, there is provided a non-invasive fixator for fixing a fracture or soft tissue injury, the fixator comprising:

first and second articulated bracelets, each of which is for location around the circumference of a patient's limb;

each articulated bracelet comprising a plurality of linking elements located in a plurality of rows, wherein said linking elements have complementary linking means to permit linking said rows of linking elements together in an interchangeably articulated or fixed relationship; and a fixed bridge connector having a fixed shape connected to the first and second bracelets and extending perpendicularly to the direction of the rows, and arranged in use to provide a force against a limb of a patient.

In some embodiments, the fixed shape may be stepped in profile, to provide a portion extending below the height of the bracelets.

In some embodiments, the fixed bridge connector comprises a first rod extending between the first and second bracelets, and affixed to each bracelet, in combination with a further rod affixed to the first rod and arranged perpendicularly thereto; the further rod having a footplate extending generally parallel to the first rod and arranged, in use, to contact the limb of a patient. The height of the footplate may be adjustable, for example by altering the relative location of the further rod with respect to the first rod. In embodiments, the first rod may be affixed to the bracelets via connector elements and/or connecting devices as described herein. Alternatively, the rod may include fittings such as screws, bolts, clips, etc allowing such fixing directly to the bracelet. In embodiments, the further rod may be affixed to the first rod via a connecting device as described herein. This may allow the height of the footplate to be adjusted by moving the rod with respect to the connecting device. Alternatively, the further rod may be threaded and received within a corresponding threaded opening in the first rod; the height may then be adjusted by rotation of the relevant pieces. In some instances, this rod arrangement may be used with prior art fixators (for example, as described in WO2010/094971).

DETAILED DESCRIPTION OF THE INVENTION

Figure 1:
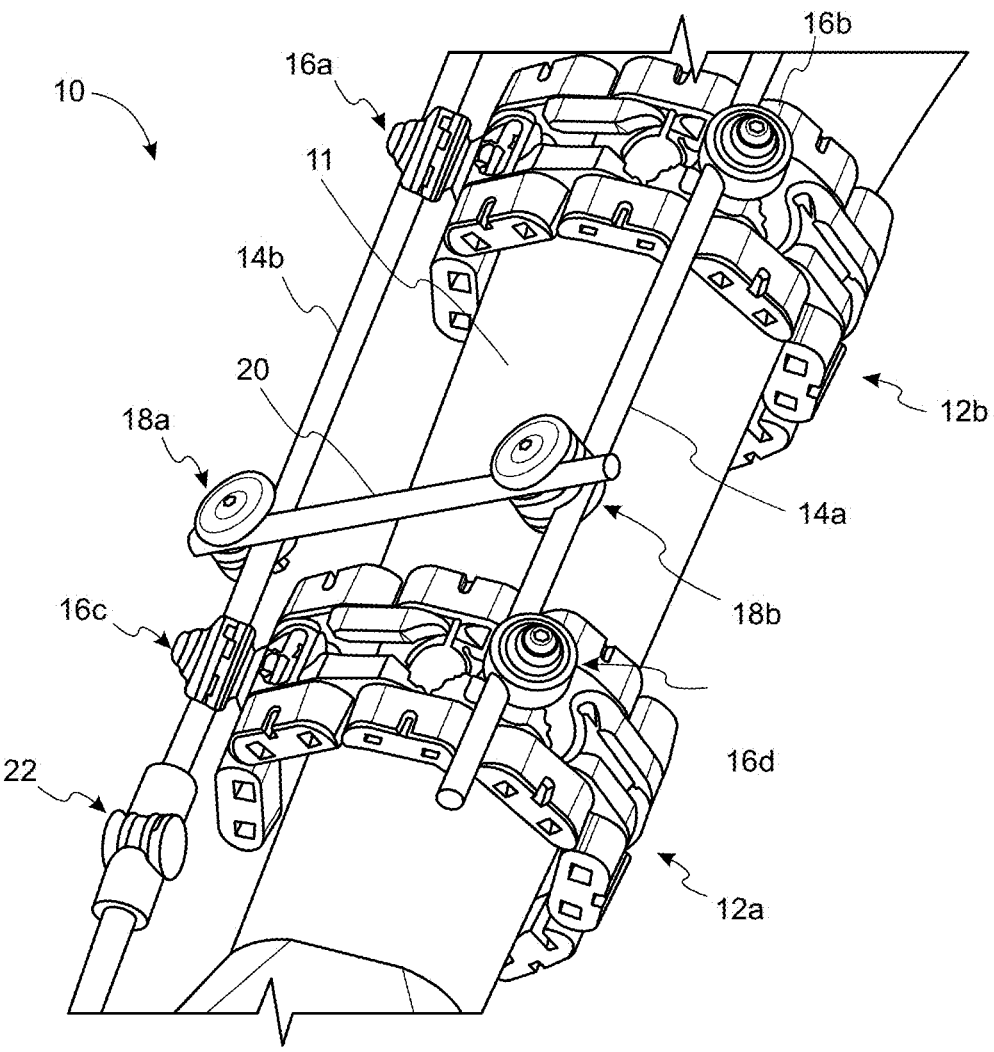
FIGS. 1 and 2 illustrate prior art fixators from WO2010/094971.
Figure 2:
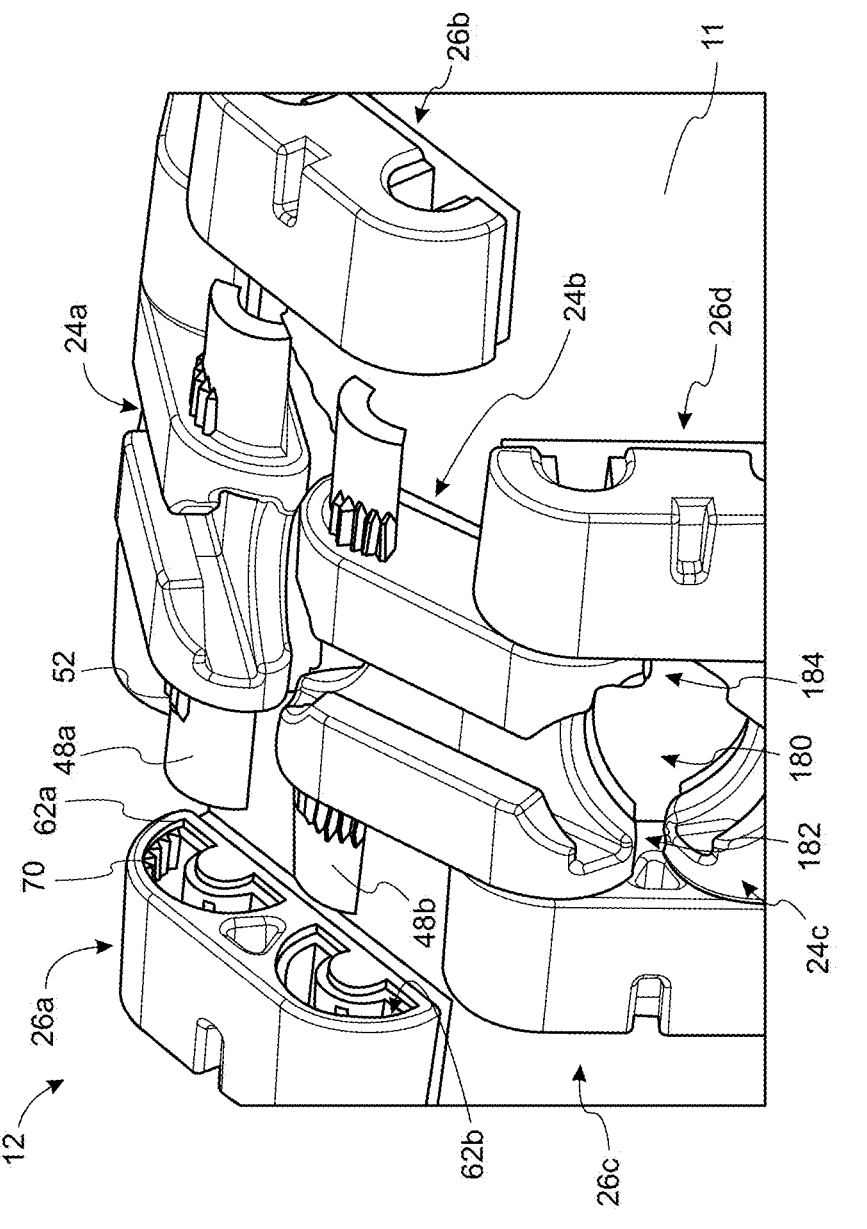

It is useful here to describe the features of the prior art fixator device, as many of the features of the present invention are to some degree related. FIGS. 1 and 2 illustrate the prior art device; FIG. 1 showing a perspective view of a fixator mounted on a patient's arm, and FIG. 2 showing a detail of a bracelet in an almost assembled state.

FIG. 1 shows a non-invasive fixator 10 mounted on an arm 11 of a patient. The fixator 10 comprises two bracelets 12a, 12b that are maintained in relative positions on the arm by two approximately parallel running rods 14a, 14b, which are secured to the bracelets by means of four connecting devices 16a, 16b, 16c, 16d (two at each bracelet). A third rod 20 is secured crosswise by two cross-linking devices 18a, 18b. A hinging device 22 is connected at one end of rod 14b. The hinge device is connected by means of a rod to another bracelet or a cuff. Thus, the fixator may comprise three bracelets. The hinge device is aligned with the plane of the joint, adjacent to fracture zone movement.

The bracelets 12 are comprised of a plurality of linking elements arranged in rows. In the configuration shown in FIG. 1, the elements are arranged in three rows: a central row and two outer rows. This is illustrated in more detail in FIG. 2, which shows a portion of a bracelet in an almost assembled state. Here, the central row is comprised of linking elements 24 having projections 48 with the two outer rows being comprised of linking elements 26 having slots 62.

In FIGS. 1 and 2, each element of the central row links to two elements of the each of the adjacent outer rows, so that elements of adjacent rows are offset relative to one another. Thus, linking element 24b having projections is in a fixed articulated relationship with linking element 26c having slots of the left-hand outer row and linking element 26d of the right-hand outer row, and is about to be linked to linking elements 26a and 26b, to complete the left- and right-hand outer rows.

Visible in FIG. 2 are the ridge-like teeth 70 formed on an inner arcuate surface of slot 62a of linking element 26a, for engaging with ridge-like teeth 52 on an upper arcuate surface of projection 48a of linking element 24a. Here, it is briefly noted that the ridge-like teeth 70, 52 are complementary and when engaged with each other permit linking elements 26a and 24b to be linked in a fixed relationship. Thus, the bracelet can be placed around a user's limb with the linking elements unlinked (so the bracelet is flexible), and once in position, the linking elements are assembled so as to fix the relative positions and lock the bracelet in place.

Figure 3:
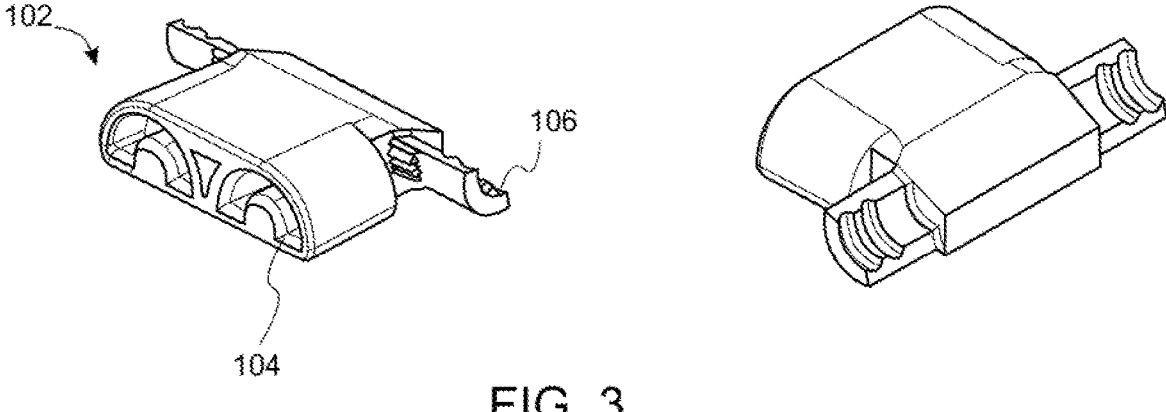
FIG. 3 shows a T-piece connector element.

Turning now to FIG. 3, this shows a T piece connector element 102 for use with a fixator as described. The connector element 102 includes arcuate slots 104 which are designed to engage with arcuate projections of linking elements of each bracelet, such that the connector element 102 can replace a linking element in each bracelet. The connector element 102 also include a pair of arcuate projections 106 extending perpendicularly to the axis of the arcuate slots 104.

Figure 4:
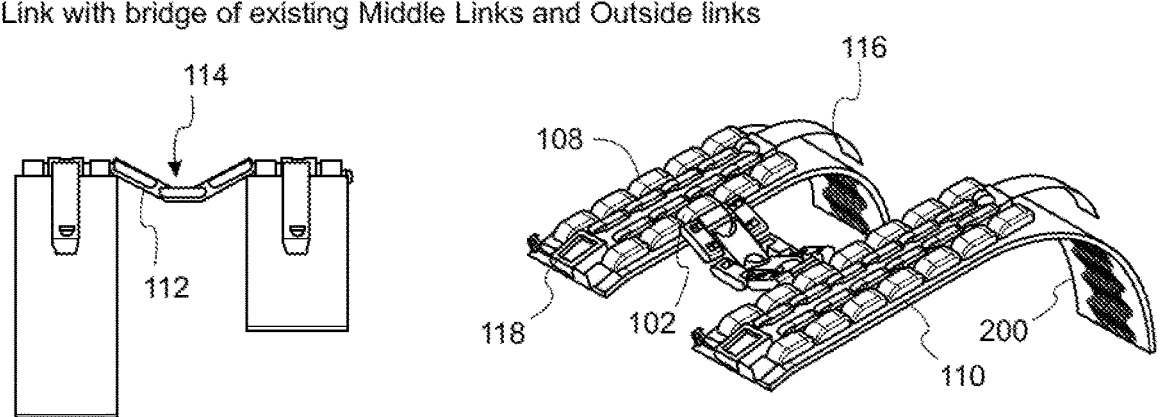
FIG. 4 shows two bracelets connected via a bridge and T-piece connector elements.

In use, the connector element 102 can be integrated into bracelets as shown in FIG. 4. The connector element 102 replaces a linking element in each bracelet 108, 110, such that the arcuate projections 106 extend parallel to but laterally displaced from the direction of the rows of linking elements in the bracelets 108, 110. These projections can then be used to link to further linking elements 112 to connect the bracelets to one another, the further linking elements 112 forming a bridge 114. The elements 112 of the bridge 114 may then be adjusted so as to adopt a form which, in use, will provide a force urging against the patient's limb. Using the same linking/locking technique as the linking elements of the bracelets 108, 110, the bridge may be fixed in position and shape once suitable.

Also shown in FIG. 4 are two further features of the fixator. Each bracelet 108, 110 includes a ratcheted tongue 116 and slot 118 combination, whereby the tongue 116 may be inserted into the corresponding slot 118 but not easily removed. This feature may be used to adjust the diameter of the corresponding bracelet for use with different size limbs, without the need to alter the bracelet itself (for example, in terms of number of linking elements). This can also prevent accidental removal of the bracelets.

The second further feature is a polylattice membrane 200 located within each bracelet; this is described in more detail later.

Figure 5:
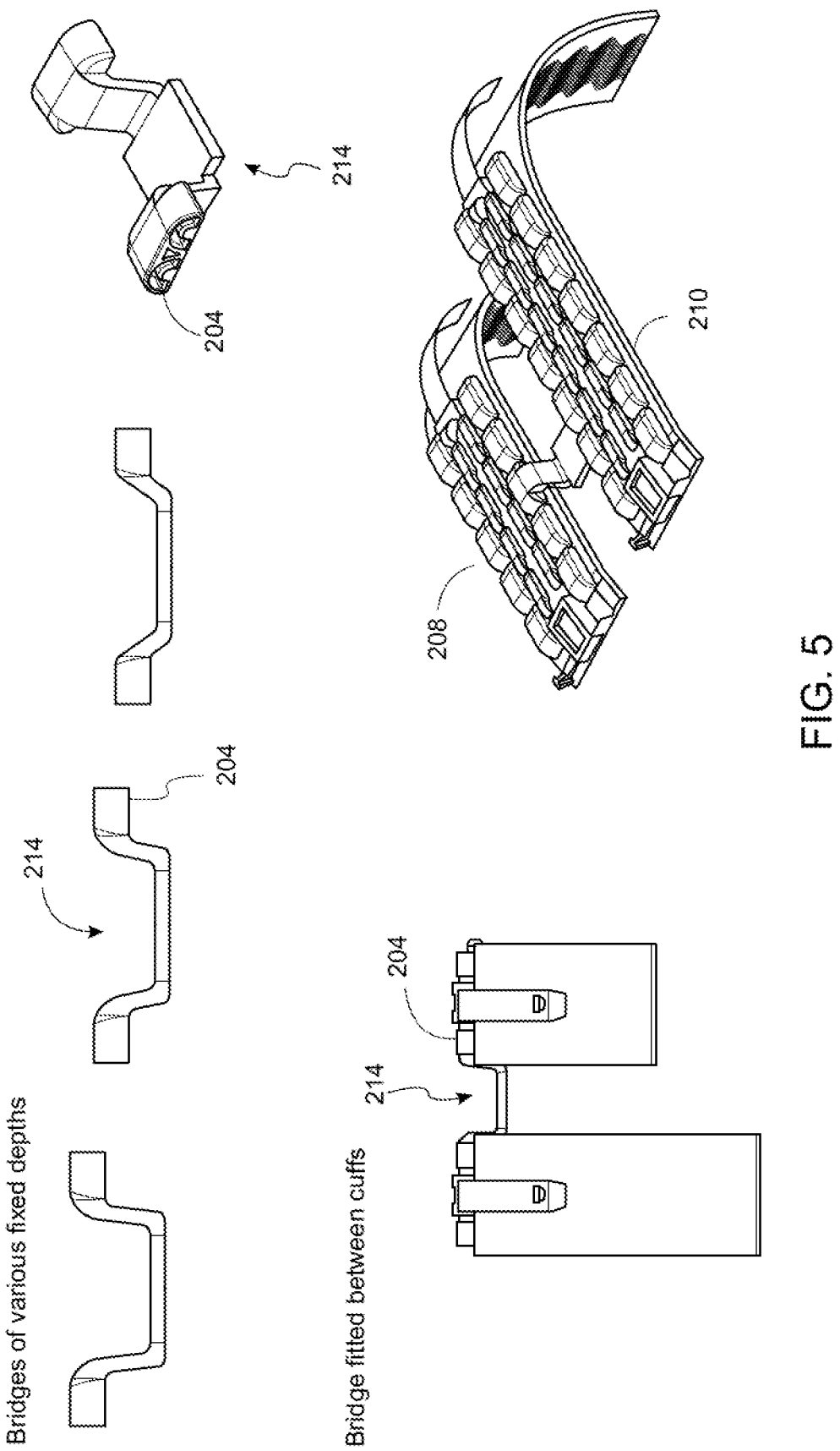
FIG. 5 shows various fixed bridge pieces, and two bracelets connected via a fixed bridge.

An alternative bridge arrangement is shown in FIG. 5. Here the bridge 214 takes the form of a fixed piece having a stepped profile to provide the required lowered portion which in use will apply force to a user's limb. The bridge 214 includes a pair of arcuate slots 204 which will engage with corresponding arcuate projections on the linking elements 212 of the bracelets 208, 210.

Figure 6:
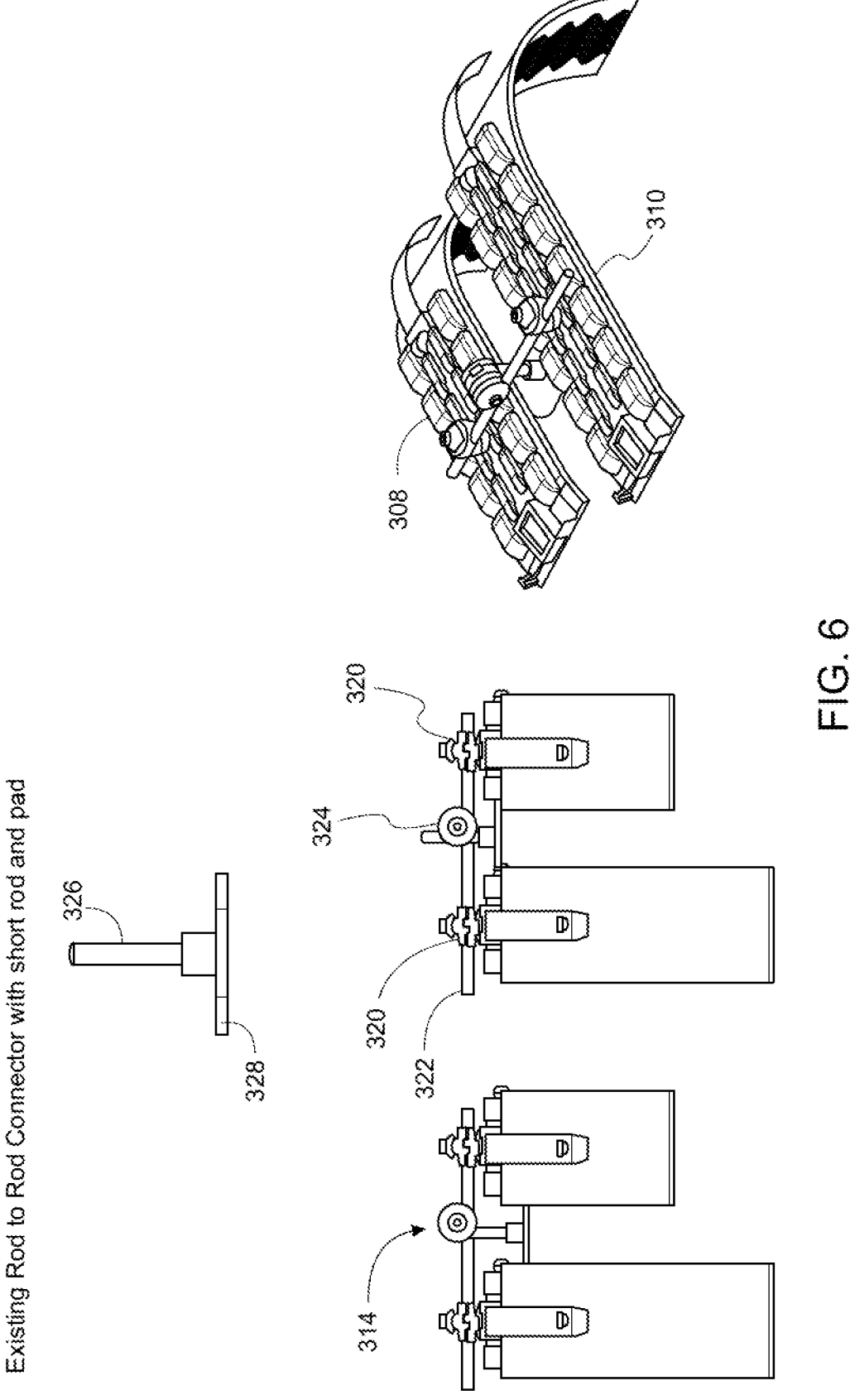
FIG. 6 shows a fixed bridge piece formed from rods and connecting devices, and two bracelets connected via the fixed bridge.

A further variant bridge arrangement is shown in FIG. 6. This bridge 314 is formed from multiple parts: a pair of connecting devices 320, each of which engages with one of the bracelets 308, 310, and which between them are secured to a rod 322 extending between the bracelets. A further rod-rod connector 324 is secured to the rod 322 and connects a second, perpendicular rod 326 to the first rod. The perpendicular rod 326 carries a footplate 328 which in use applies the desired pressure to the patient's limb. The height of the footplate 328 can be varied by adjusting the perpendicular rod 326 within the rod-rod connector 324. The two connectors are described below in more detail with reference to FIGS. 8 and 9.

Figure 7:
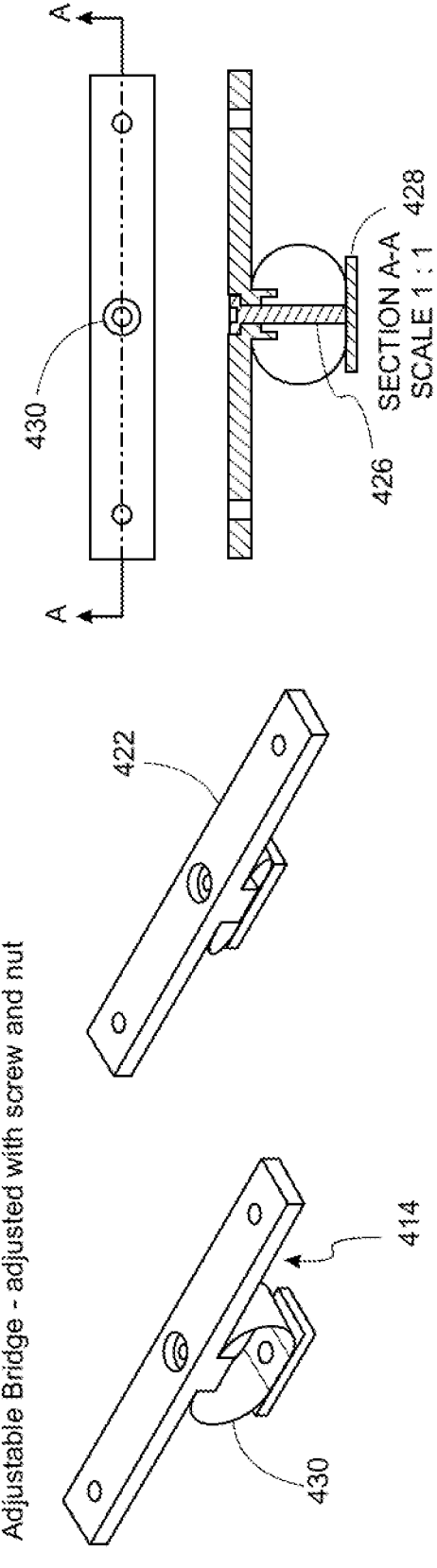
FIG. 7 shows an alternative fixed bridge piece, and two bracelets connected via the fixed bridge.
Figure 7:
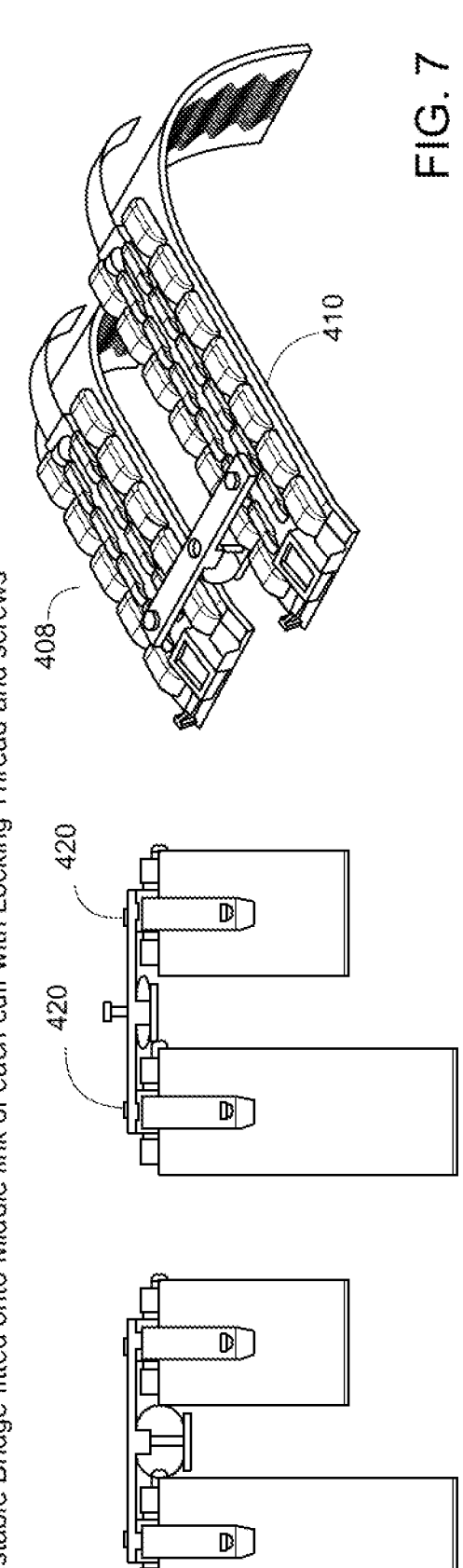

A yet further bridge variant is shown in FIG. 7. This bridge 414 consists of a flattened crossbar 422 which is fastened directly to the bracelets 408, 410 via locking screws 420. A perpendicular rod 426 and footplate 428 are mounted within a threaded aperture 430 on the crossbar 422. As the rod 426 is correspondingly threaded, the height of the footplate can be simply adjusted as required. Flexible sprung strips 430 can be provided extending between the crossbar 422 and footplate 428 to assist adjustment and to retain the rod 426 and footplate 428 in position.

Each of the bridge variants shown in FIGS. 4-7 may be used together with bracelets as described herein (or as described in earlier application WO2010/094971) to link the bracelets together and allow for application of pressure or force to the limb of a user.

Figure 8:
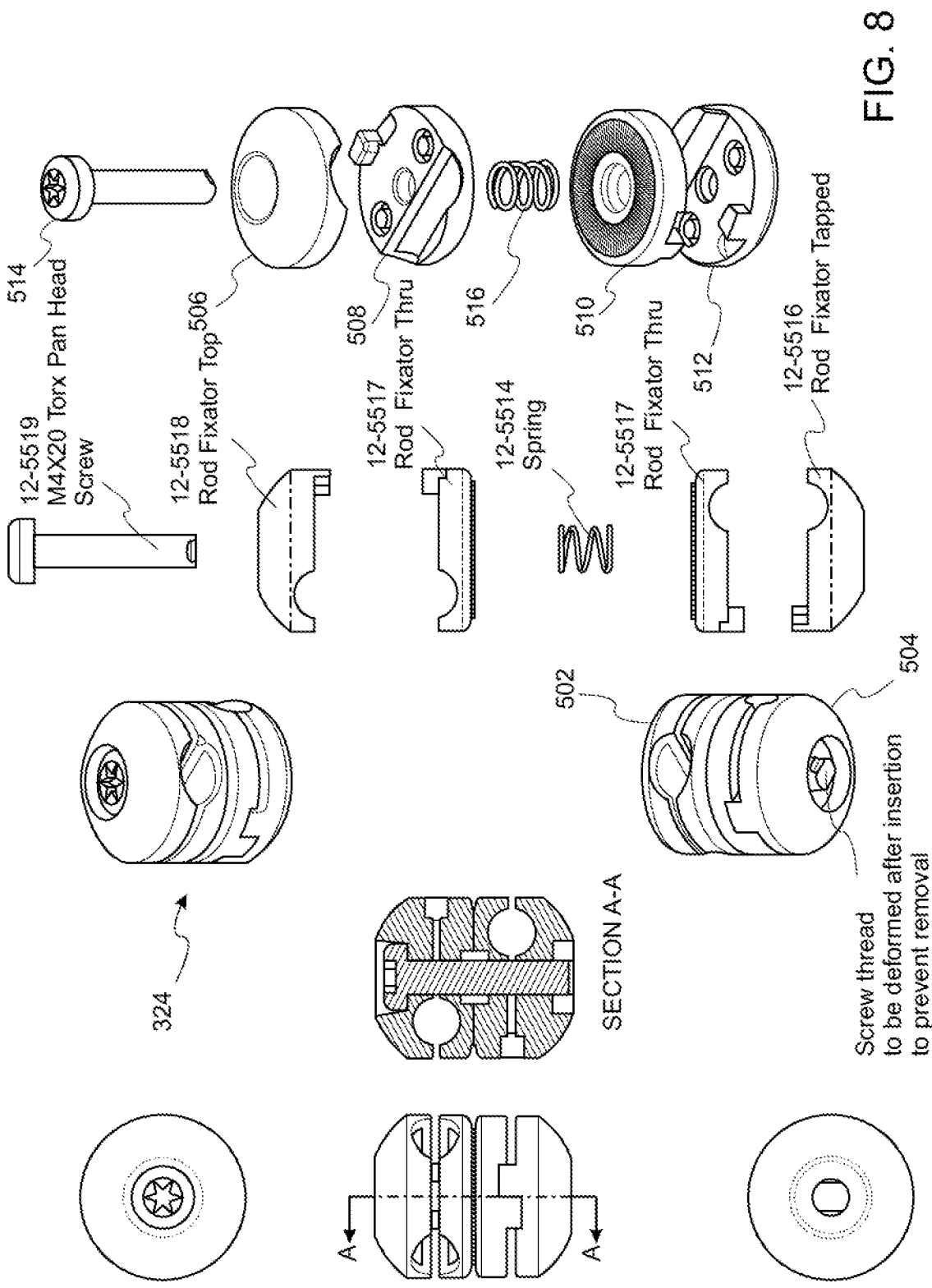
FIG. 8 shows a connecting device for use in connecting a rod to a rod.
Figure 9:
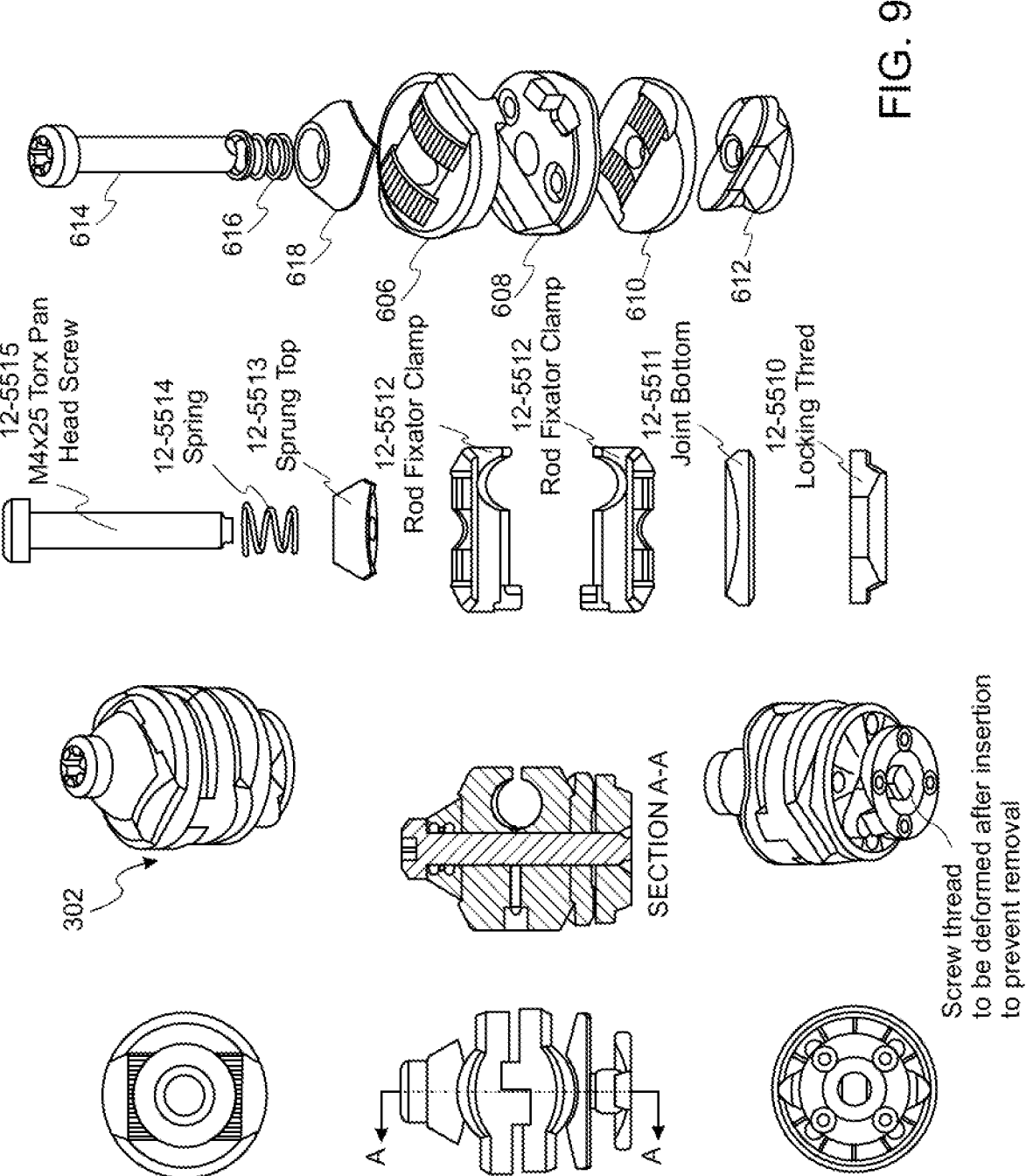
FIG. 9 shows an articulated connecting device for use in connecting a rod to a bracelet.

The connectors described above with reference to FIG. 6 are shown in more detail in FIGS. 8 and 9. These are similar to those described in the earlier application WO2010/094971. A rod-rod connector 324 is shown in FIG. 8. This consists of two cooperating portions 502, 504 each being able to receive a rod of appropriate dimensions. The cooperating portions 502, 504 are each themselves formed from two sub-pieces 506, 508, 510, 512 which together form a suitable space to receive the rod. The components are all held together by a screw 514 and spring 516 extending through a central axis, with the screw 514 thread being deformed after assembly to prevent removal. The spring 516 is arranged to urge the cooperating portions 502, 504 apart against the resistance provided by the screw 514. The sub-pieces 508, 510 forming the contacting surfaces of the cooperating portions 502, 504 are patterned with, for example, a series of radial ridges and grooves, to provide resistance to relative movement as well as tactile feedback when adjusting the positions of the cooperating portions.

A rod-bracelet connector 320 is shown in FIG. 9. As with the rod-rod connector 324, this includes a number of sub-pieces held together by a screw 614 and spring 616. In this case, however, only two sub-pieces 606, 608 form a suitable space for receiving a rod of appropriate dimensions. These sub-pieces also include partially-cylindrical ridge-and-groove patterned portions which cooperate with corresponding recessed patterned portions provided on sub-pieces 610, 618. Together these allow the rod-holding sub-pieces 606, 608 to be angled so as to align the held rod at a desired angle. The lowermost sub-portion 612 includes a shaped section designed to engage with an element of the bracelets—see, for example, FIGS. 1 and 2 showing a rod-bracelet connector being inserted into appropriately-shaped openings provided on the bracelets. In this example, the sub-pieces 606, 608 include projections and detents to restrict relative rotation of the sub-pieces, as do the corresponding sub-pieces of the connector of FIG. 8.

Figure 10:
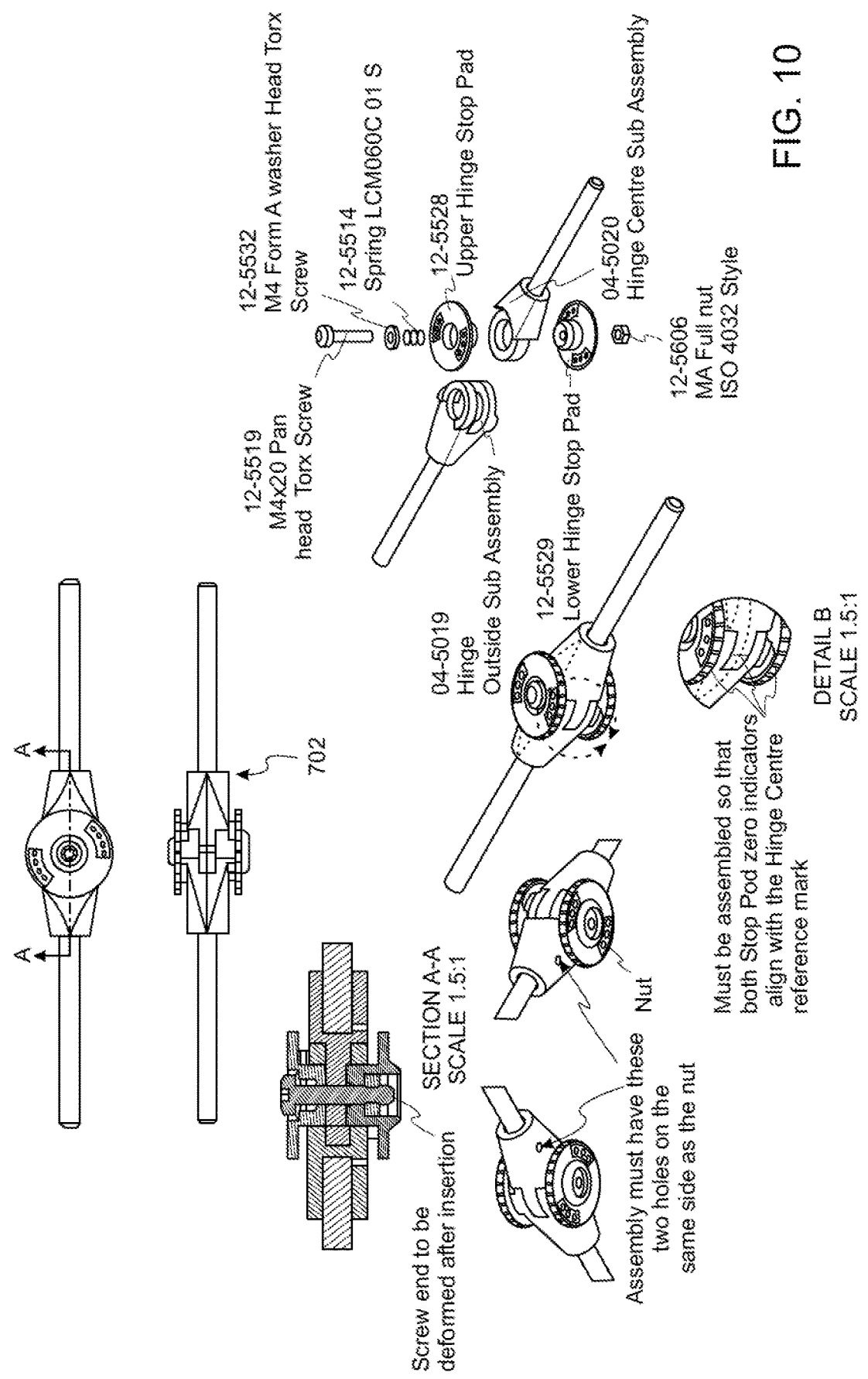
FIG. 10 shows a hinge device for providing a rod with articulation.

FIG. 10 shows a hinge joint which may be used to connect rods mounted to the bracelets, in order to allow for mobility of a limb joint, or to connect rods in other than a straight line. A hinge joint 702 has a first part hinged to a second part, by means of a third part comprising upper and lower stop pads and a nut-and-bolt assembly. The first part has a cylindrical body with two rings which are spaced apart to receive a ring of the second part. The rings have cooperating teeth/ridges which engage with one another to provide tactile feedback and resistance to movement. The arc of rotation can be limited by means of protrusions defined on the various components. Rods are received within each of the first and second parts; the receiving portion may be shaped differently in cross-section from the rods to provide a secure fit (eg, a round rod may be received in a polygonal opening).

Figure 11:
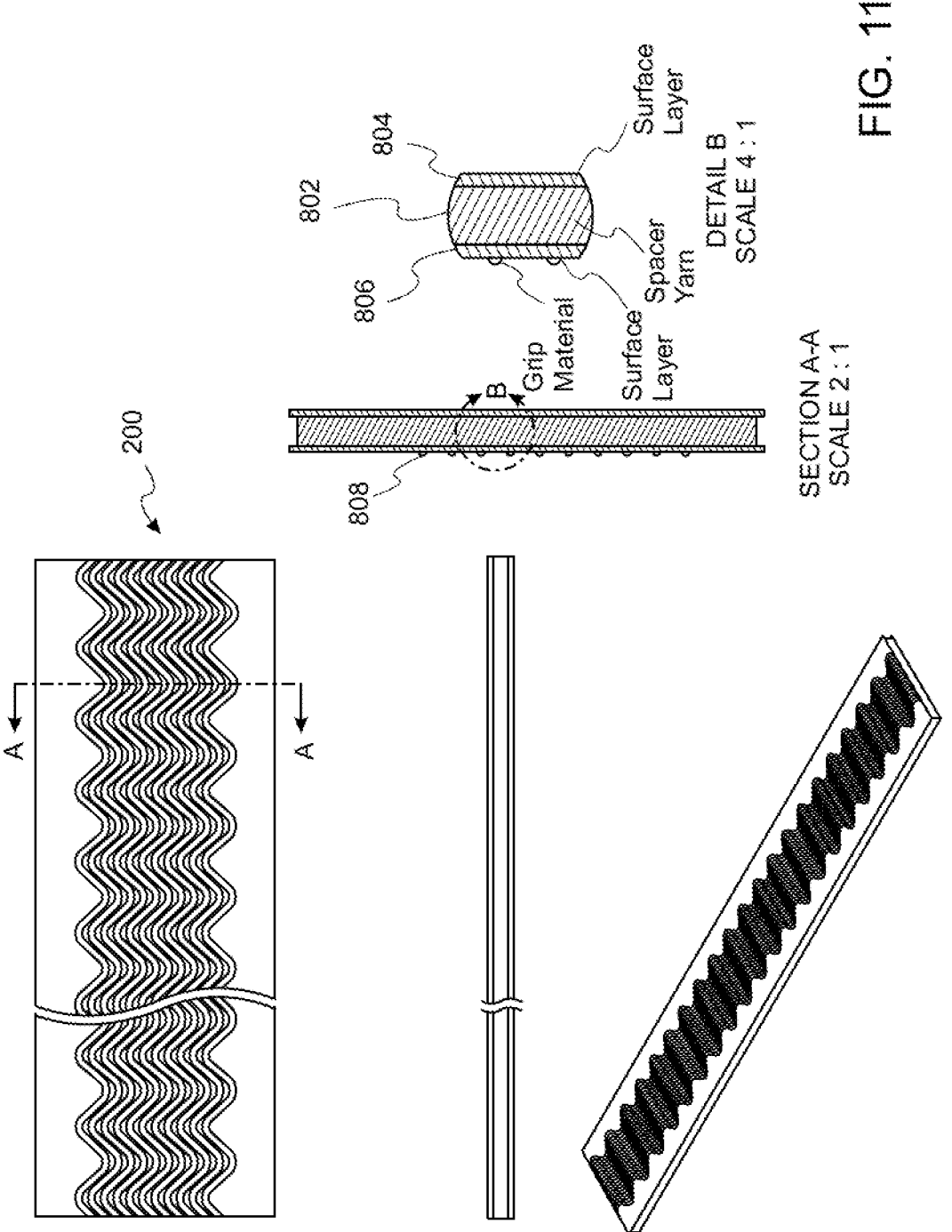
FIG. 11 shows a polylattice membrane cushioning fabric.

Finally, FIG. 11 shows a cushioning fabric 200 in the form of a polylattice membrane comprising a non-woven spacer yarn layer 802 disposed between outer surface fabric layers 804, 806. The spacer layer 802 comprises yarn threads extending generally but randomly between the outer layers so as to provide a cushion effect. The surface layers in this embodiment are each 1 mm thick, while the spacer layer is 4 mm thick. The yarn threads of the spacer layer are formed of clinical grade polypropylene of around 0.1 mm diameter. The surface layers are knitted or woven texturised polyester/polyamide mix of around 10 wales or courses per cm. The polylattice membrane further includes a silicone grip material 808 disposed on the outside of one of the surface layers, to improve adhesion to a user's limb. The grip material is patterned to further improve adhesion.

Thus, the various elements of the described fixator combine to provide an improved external fixator which may be used in combination with a bridge piece (of various possible forms) which can serve to apply pressure to a user's limb at an appropriate point. Further, the novel connector element allows for additional components to be connected to the bracelets using a similar system to the linking elements of the bracelets. The cushioning fabric improves patient comfort.

The invention claimed is:

1. A non-invasive fixator for fixing a fracture or soft tissue injury, the fixator comprising:
    first and second articulated bracelets, each of which is for location around the circumference of a patient's limb;
    each articulated bracelet comprising a plurality of linking elements located in a plurality of rows, wherein said linking elements comprise a means for linking said linking elements within a row and across adjacent rows together in an interchangeably articulated or fixed relationship;
    at least one linking element in each bracelet comprising a connector element having a portion extending laterally from one of said rows, and forming a further linking means to permit linking of further elements to the bracelet extending between the first and second bracelets in a direction generally perpendicular to the direction of the rows.

2. The fixator of claim 1, wherein the connector element comprises a T-piece.

3. The fixator of claim 1 further comprising additional linking elements connected to the connector element to form a bridge extending between the first and second articulated bracelets.

4. The fixator of claim 3 wherein the additional linking elements each comprise complementary linking means to permit linking said linking elements together in an interchangeably articulated or fixed relationship.

5. The fixator of claim 3 wherein the linking elements of the bridge are arranged and fixed in position so as to extend between and below the first and second bracelets such that when worn on a limb the bridge will provide pressure against the limb.

6. The fixator of claim 1 wherein the bracelets each comprise an adjustable closure, preferably comprising a toothed strip which engages with a corresponding ratcheted fastener to secure the bracelet in a closed loop.

7. The fixator of claim 1 comprising a fixed bridge connector having a fixed shape connected to the first and second bracelets and extending perpendicularly to the direction of the rows, wherein the fixed shape is stepped in profile, to provide a portion extending below the height of the bracelets.

8. The fixator of claim 7 wherein the fixed bridge connector is connected to the bracelets via connector elements.

9. The fixator of claim 7 wherein the fixed bridge connector replaces at least one linking element in at least one bracelet.

10. The fixator of claim 1 comprising a bridge connector having a first rod extending between the first and second bracelets, and affixed to each bracelet, in combination with a further rod affixed to the first rod and arranged perpendicularly thereto; the further rod having a footplate extending generally parallel to the first rod and arranged, in use, to contact the limb of a patient to provide pressure against a limb of a patient at a location between said first and second bracelets.

11. The fixator of claim 10 wherein the height of the footplate is adjustable.

12. The fixator of claim 10 wherein the first rod is affixed to the bracelets via said connector element.

13. The fixator of claim 10 wherein the first rod includes fittings selected from the group of screws, bolts, and clips allowing fixing of the first rod directly to the bracelet.

14. The fixator of claim 10 wherein the further rod is affixed to the first rod via a connecting device.

15. The fixator of claim 10 wherein the further rod is threaded and is received within a corresponding threaded opening in a rod to rod connector to connect it to the first rod.

16. The fixator of claim 1 further comprising a cushioning fabric disposed within one or more of the bracelets, and arranged to, in use, contact a patient's limb.

17. The fixator of claim 16, wherein the cushioning fabric is a polylattice membrane comprising a non-woven spacer yarn layer disposed between outer surface fabric layers.

18. A non-invasive fixator for fixing a fracture or soft tissue injury, the fixator comprising:

first and second articulated bracelets, each of which is for location around the circumference of a patient's limb;

each articulated bracelet comprising a plurality of linking elements located in a plurality of rows, wherein said linking elements comprise means for linking said linking elements within a row and across adjacent rows together in an interchangeably articulated or fixed relationship; and a fixed bridge having a fixed shape connected to and extending between the first and second bracelets and extending perpendicularly to the direction of the rows, and arranged in use to provide pressure against a limb of a patient at a location between said first and second bracelets.

19. The fixator of claim 18 wherein the fixed shape is stepped in profile, to provide a portion extending below the height of the bracelets.

20. The fixator of claim 18 wherein the fixed bridge connector comprises a first rod extending between the first and second bracelets, and affixed to each bracelet, in combination with a further rod affixed to the first rod and arranged perpendicularly thereto; the further rod having a footplate extending generally parallel to the first rod and arranged, in use, to contact the limb of a patient to provide pressure against a limb of a patient at a location between said first and second bracelets.

21. The fixator of claim 20 wherein the height of the footplate is adjustable.

* * * * *